Figure 1:
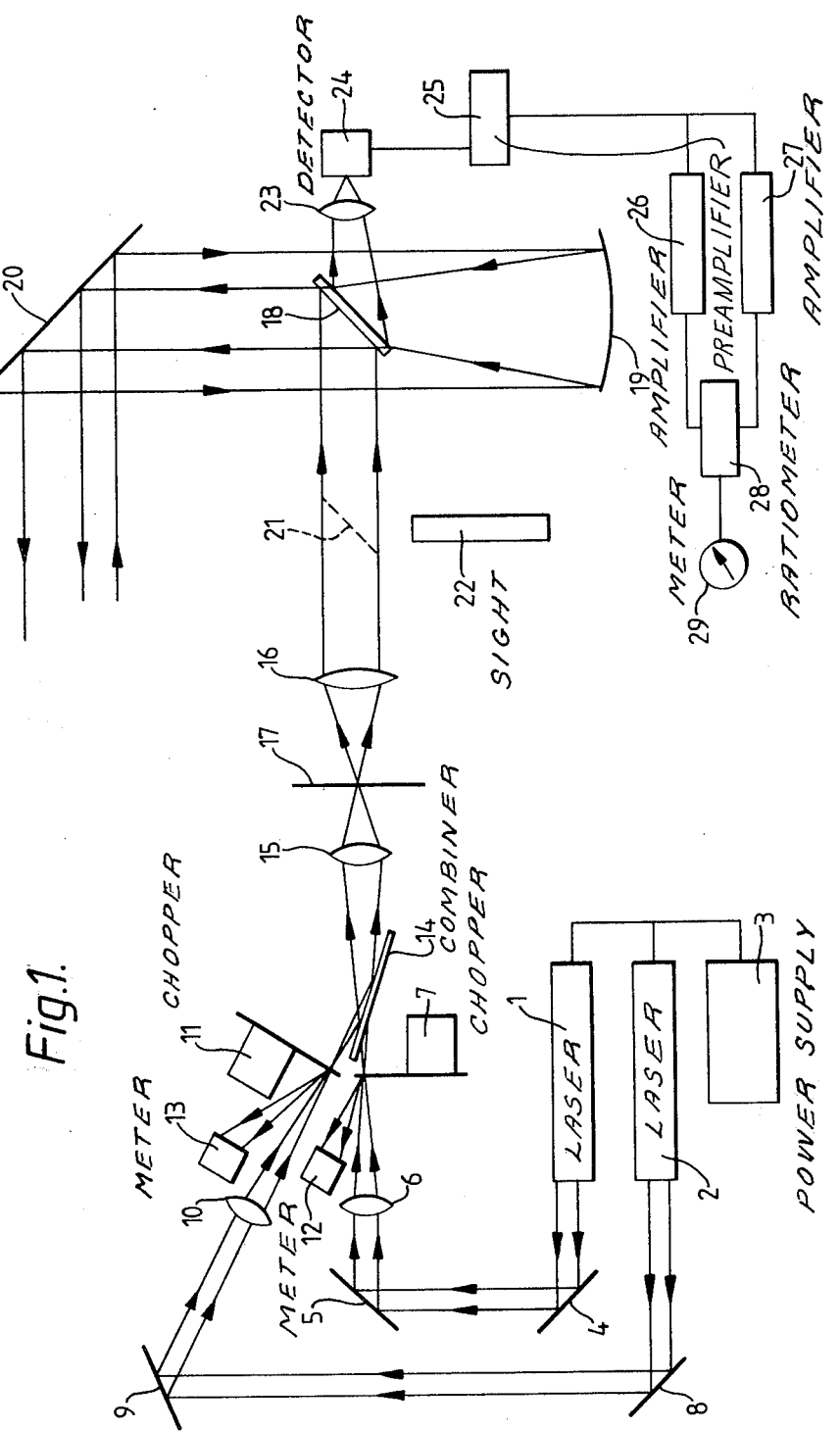

United States Patent [19]

Becconsall et al.

[11] 4,426,640
[45] Jan. 17, 1984

[54] LASER SCANNING APPARATUS

[75] Inventors: Jack K. Becconsall, Appleton; John H. W. Cramp, Lymm; Robert F. Reid, Beechwood; Reginald C. Moore, Harpenden; Barry J. Rye, Cottingham; Eric L. Thomas, Cherry Burton, all of England

[73] Assignee: Imperial Chemical Industries Limited, London, England

[21] Appl. No.: 184,259

[22] Filed: Sep. 5, 1980

[30] Foreign Application Priority Data

Sep. 5, 1979 [GB] United Kingdom ................ 7930707

[51] Int. Cl.$^3$ ............................................ G08B 17/10
[52] U.S. Cl. .................................. 340/632; 250/339; 356/323; 356/437
[58] Field of Search ................ 250/339; 356/323, 325, 356/407, 437; 340/632, 525; 346/107 R, 108, 14 R

[56] References Cited

U.S. PATENT DOCUMENTS

| 2,930,893 | 3/1960 | Carpenter et al. ................ 250/339 |
| 3,521,958 | 7/1970 | Treharne ...................... 356/323 X |
| 3,619,057 | 11/1971 | Castellano et al. ............. 356/325 X |
| 3,761,715 | 9/1973 | Menzies ........................ 250/338 |
| 3,766,380 | 10/1973 | Menzies ........................ 250/343 |
| 3,998,557 | 12/1976 | Javan ........................... 356/205 |

OTHER PUBLICATIONS

Journal of Applied Physics, vol. 46, No. 7, Jul. 1975, W. B. Grant and R. D. Hake, Jr., pp. 3019-3023, GP Elliott Brochure.

Primary Examiner—John W. Caldwell, Sr.
Assistant Examiner—Daniel Myer
Attorney, Agent, or Firm—Cushman, Darby & Cushman

[57] ABSTRACT

Apparatus for monitoring gaseous pollutants (e.g. on a chemical plant) produces two infra-red laser beams having different wavelengths (one corresponding to an absorption line of the gas to be monitored, the other being a reference) which are modulated with different frequencies or phases, and then combined into a single scanning beam. The scanning beam is continuously displaced angularly so as to scan the area to be monitored. A portion of the beam is returned to the apparatus by scattering or reflection, and is measured. By correlating this with the direction of the beam, a plan of the monitored area superimposed with a continuously updated indication of the amount of gas can be displayed e.g. on a VDU.

16 Claims, 2 Drawing Figures

LASER SCANNING APPARATUS

The present invention relates to an apparatus for the remote monitoring of gases and in particular to an apparatus for the remote monitoring of gaseous pollutants in an atmospheric environment, for example in chemical plants.

There is a need to carry out remote monitoring of gaseous pollutants, for example toxic or inflammable gases, within industrial locations, such as in chemical plants. In particular, there is a need to obtain rapid and continuous measurements of the concentration of gaseous pollutants over a large area and to ensure that the measurements are continually updated. This is especially important with regard to plant safety when toxic or inflammable gases are involved, for example in the detection of ethylene leaks in a polyethylene plant where explosive mixtures of ethylene and air could result. At present leaks may be detected by an array of individual sensors distributed over the area, but because gas at high pressure emerges as a narrow plume from any small hole, the gas can miss all the detectors until it is too late.

Most of the undesirable gases absorb electromagnetic radiation at wavelengths which can readily be matched by lasers, and various methods of measuring small amounts of such gases using lasers have been proposed for a variety of situations. However, none of those methods or apparatus could be applied entirely satisfactorily to the continuous monitoring of pollutants over a wide area, e.g. through lack of robustness, an inability to identify where a leak is occurring within the wide area, or through lack of sensitivity.

According to one aspect of the present invention we provide an apparatus for remote quantitative monitoring of one or more selected gases in a gaseous environment, which comprises laser sources for generating electromagnetic radiation capable of being tuned to give at least one detection beam containing a specific absorption wavelength of the gas or gases to be monitored and at least one reference beam having a wavelength that is significantly less strongly absorbed by the gas or gases to be monitored, means for modulating the amplitude of each of the beams with different modulation frequencies or phases, means for combining the modulated beams into a single combined beam in which the component modulated beams are substantially coincident with one another, scanning means to displace the combined beam angularly through the gaseous environment so as to direct the combined beam towards a plurality of locations sequentially and repetitively, means for collecting at least a portion of the radiation which is returned from each of the locations, a detector for deriving electrical signals corresponding to the intensity of the collected radiation, means for isolating the electrical signals corresponding to the intensity of radiation having the aforesaid modulation frequencies or phases, means for obtaining the ratio of the isolated signals corresponding to radiation collected from a detection beam and a related reference beam thereby to provide a measure of the amount of the selected gas or gases in each beam path traversed between the apparatus and the scanned locations, and means for indicating the amount of gas detected.

While it may be possible to divide a single laser beam to provide the sources for the detection and reference beams, it is preferred to use a separate laser for each beam.

The light emerging from a pulsed mode laser is already modulated in that it emerges in the form of pulses of a predetermined frequency. In such lasers the means for modifying the amplitudes of the beams thus forms an integral part of the laser itself. The different modulations for the detection and reference beams are obtained by having lasers whose pulse-rates are different. However, we find that in the current state of the art, continuous mode gas lasers are more able to withstand use over long periods under the rugged conditions of industrial environments, and accordingly they are preferred as the laser sources for both detection and reference beams, even though they require the provision of separate modulating means. The lasers particularly preferred are continuous mode gas lasers which are capable of being tuned to selected discrete wavelengths in the infra-red corresponding to absorption wavelengths of the gas or gases to be monitored. Infra-red laser light has the advantage, as compared to visible laser light, of not affecting the retina of the human eye and hence being safe in this respect. Moreover, infra-red light, in having a longer wavelength than visible light, penetrates better through wet, smokey and dusty industrial environments, thus giving infra-red lasers a greater range, enabling them more readily to monitor locations hundreds of metres away.

Suitable discretely tunable gas lasers include carbon dioxide $C^{12}O_2^{16}$, e.g. for monitoring ozone, ammonia, vinyl chloride, fluorocarbons and unsaturated compounds such as ethylene; carbon dioxide $C^{12}O_2^{18}$ e.g. for the monitoring of sulphur dioxide; carbon dioxide $C^{14}O_2^{16}$ e.g. for phosgene or ethylene oxide; helium-neon (at 3.39 $\mu$m) e.g. for monitoring methane, and carbon monoxide lasers for monitoring carbon monoxide. The only gases having no absorption in the infra-red are homonuclear diatomic gases, such as chlorine, and monatomic gases such as mercury, so it will be appreciated that the wide range of tunable gas lasers available enables the apparatus of the invention to be used to monitor a wide range of commonly occurring pollutants in the atmosphere. The carbon dioxide lasers are tunable to wavelengths which avoid the absorption bands of water and carbon dioxide, and hence are a range of lasers particularly suited to the present application.

In the plant environment where a variety of scattering surfaces are encountered, it is preferable that the wavelengths of the detection and reference beams be close together in order to reduce the effect of differential albedo. Thus the difference in wavelengths of the two beams is preferably less than 0.1 $\mu$m, where suitable absorption bandstrengths are available.

The preferred means for modulating the beams from continuous mode gas lasers is a rotatable sector chopper, which, when rotated in the path of a laser beam, intermittently interrupts the beam at a frequency dependent on its rate of rotation. The detection and reference beams are preferably passed through different choppers rotating at different speeds so as to modulate them with different frequencies, or through a two-frequency chopper. Alternatively, the two beams, while still separated, may be passed through the same chopper so that they are interrupted at different times, the beams thereby being modulated at the same frequency, but with different phases. Other ways of modulating laser beams include the use of acousto-optic and electro-optic means.

Modulation of a continuous mode laser can also be carried out within the laser, e.g. by modulating the discharge or by using physical means within the laser rather than externally as described above.

The beams, preferably one detection beam and one reference beam, are conveniently combined using a slab of infra-red transparent material, for example germanium (or sodium chloride or zinc selenide etc.). This is preferably mounted such that the two laser beams will strike opposite sides of the slab at the Brewster angle with mutually perpendicular planes of polarization, whereby one beam will be transmitted and the other will be predominantly reflected to form two substantially coincident beams distinguishable by their different modulations. It is an advantage of this method of combining the beams that, for a slab mounted in a vertical plane, about 99% of the horizontally-polarized beam may be transmitted and about 70% of the vertically-polarized beam reflected, thereby allowing combination of the beams coaxially with minimum loss of power. Thus each beam may be passed along exactly the same path through the same absorption materials and return to the same detector, preferably to exactly the same portion of the detector. However, the term "substantially coincident" may include beams which are for example close together and parallel so that they pass through or strike closely adjacent regions.

The simplest form of scan is one wherein the locations are aligned and are sufficiently narrow to fall within the width of the beam, the scan then being effected simply by movement of the beam to and fro in a single arcuate sweeping movement. This simple scan is suitable for monitoring pipe lines, for example, which may run transverse or parallel to the beam direction. However, this does not fully utilize the potential scope of the apparatus, and a preferred scanning means is one which is moveable in at least two directions so as to direct the combined beam at locations which are spread over an area whose dimensions in any two perpendicular directions are greater than the width of the beam. The area can then be covered by a raster scan.

The preferred scanning means comprises a mirror mounted within the path of the combined beam and moveable angularly relative to the incident combined beam so as to direct the beam towards different locations when such angular movement occurs. The mirror must have high reflectivity at the wavelengths used, gold plated or polished stainless steel surfaces being particularly suitable for wavelengths in the infra-red. By moving only a mirror, the mass of moveable material is much less than if, for example, the lasers and ancillary equipment were also moved, and scanning can therefore be achieved more rapidly with less energy. It is preferable for the scanning means to incorporate means for cleaning the surface of the mirror in order to minimize back scatter in a dusty environment. Suitable cleaning means include windscreen wipers, heaters, electrostatic means and airblasts, for example. Where the detection and reference beams are closely side by side rather than being exactly aligned in the combined beams, separate mirrors for the two components can be used, but the use of a single mirror is mechanically easier and is preferred.

Radiation directed at various locations on a chemical plant, will fall on a variety of surfaces, including walls, ground, pipes and possibly trees for example, and the various surfaces will affect the radiation in different ways. In most cases it will be scattered in all directions with a proportion absorbed, and only a small portion of the scattered radiation will be returned to the apparatus for collection. In some places, however, the radiation may fall onto a specular reflector, which if correctly aligned, could reflect substantially all the radiation falling on it, back in the direction of the apparatus. As will be appreciated, it is the portion of the radiation which is returned to the collecting means which is collected whether this radiation is a small portion of scattered radiation or radiation which has been directed at the collector by a specular reflector, retroreflector or other directional means. The collecting means preferably comprises a telescope to focus collected radiation onto the detector. The telescope is preferably static to minimize moveable mass, but can as an alternative be angularly displaced in unison with the mirror or other scanning means.

A variety of detectors may be used depending on the particular laser sources being used. Suitable detectors include photo-emissive, photo-conductive and photo-voltaic detectors. When using infra-red laser beams, the returned radiation is conveniently detected by a photo-conductive or photo-voltaic detector, for example a cooled cadmium mercury telluride or lead tin telluride detector.

The components of the detector output in the form of electrical signals corresponding to the intensity of radiation having the aforesaid modulations are isolated, conveniently by use of frequency and/or phase selective amplifiers. Preferred amplifiers are lock-in amplifiers each being locked into the modulation frequency of one of the modulated beams by a signal derived from the modulating means or from a sample of the modulated beam. This enables the amplifier to follow any changes which might occur in the modulation frequency e.g. through drift. The detection system is able thereby to reject all the background radiation and the amplifier output gives the magnitude of the signals of interest, i.e. those which are due to the collected laser radiation at the two wavelengths.

The two isolated signals are preferably smoothed, conveniently by means of simple electrical circuits which are normally provided as a feature of commercial lock-in amplifiers, with a time constant which is longer than the modulation cycle times.

The power output of either of the lasers may alter without there being any change in the output of the other, e.g. due to drift in the power supply. The apparatus is therefore preferably provided with means to compensate each of the isolated signals for any fluctuations in the power output of the relevant laser e.g. by sampling the laser output and taking the ratio of isolated signal to laser output for each channel, e.g. using electronic ratiometers.

The ratio of the magnitudes of the two isolated and possibly compensated signals may be obtained by coupling them to an electronic ratiometer. In the absence of any of the gas to be monitored, the two signals fed to the ratiometer can be adjusted by an electronic balance control to be equal, that is, the ratio of the signals in this condition is unity. It will be appreciated that the absolute intensity of the collected radiation may differ widely depending on weather conditions reflectivity of the location being probed etc. Whenever the gas to be monitored is present, the detection beam signal will be attenuated and the ratio of detection beam to reference beam will be reduced.

What happens to the output of this latter ratiometer depends largely on the degree of sophistication desired for the apparatus. Thus, for example, the apparatus may only be required to sound an alarm when a predetermined quantity of gas is detected. The indicator means may then simply be an alarm system arranged to operate when the ratio of the signals exceeds a predetermined threshold, preferably with an indication of the position of the scanning means (and hence of the location being monitored) when the threshold is exceeded. This threshold can be varied over the area scanned, when appropriate, e.g. to compensate for beam path length differences or angles of incidence.

According to the Beer-Lambert law (which governs the transmission of energy through an absorbing medium) the logarithm of this ratio multiplied by a factor calculated from the known extinction coefficients for the two laser wavelengths, gives the mass of the gas being monitored in the beam at any given time. The factor may alternatively be found experimentally by placing in the detection beam a cell containing known amounts of gas. As it is the logarithm of the ratio which is proportional to the mass of gas in the beam, a logarithmic ratiometer is preferred, the output of which may be displayed on a linear scale to give the mass of gas.

The preferred indicating means comprises computing means having inputs of at least the ratio of the isolated signals (preferably compensated for laser fluctuations as described above) and the position of the scanning means, and being programmed to derive from these inputs an accessible correlation between the amounts and the positions of the selected gas or gases detected while continually updating this correlation as monitoring proceeds. The computing means preferably has a visual display unit arranged to provide a continuously updated display of the amount of gas detected throughout the area scanned. This is conveniently shown by superimposing an indication of the amount of gas detected onto a plan of the area scanned, showing for example the main topographical features of the area. The amount of gas can readily be shown on the screen as a varying level of brightness or symbols corresponding to different amounts of gas.

According to a further aspect of the present invention we provide a method for the remote quantitative monitoring of one or more selected gases in a gaseous environment which comprises the steps of generating electromagnetic radiation from laser sources to give at least one detection beam containing a specific absorption wavelength of the gas or gases being monitored and at least one reference beam having a wavelength that is significantly less strongly absorbed by the gas or gases being monitored, modulating the amplitude of each of the beams with different modulation frequencies or phases, combining the modulated beams into a single beam in which the component modulated beams are substantially coincident with one another, displacing the combined beam angularly through the gaseous environment so as to direct the combined beam towards a plurality of locations sequentially and repetitively, collecting at least a portion of the radiation which is reflected from each of the locations, deriving electrical signals corresponding to the intensity of the collected radiation, isolating the electrical signals corresponding to the intensity of the radiation having the aforesaid modulation frequencies or phases, and obtaining the ratio of the isolated signals corresponding to radiation collected from a detection beam and a related reference beam thereby to provide a measure of the amount of the selected gas or gases in each beam path traversed by the collected radiation originating from the laser sources.

In general the method is preferably carried out by angularly displacing the combined beam continuously so as to direct the beam at successive locations in a pattern wherein the beam traverses substantially parallel rows of locations sequentially and in alternate directions, the rate at which the beam traverses each row being varied with distance along the row such that the beam executes simple harmonic motion. This reduces the acceleration of the mirror, or other moveable scanning means used to direct the combined beam, at the ends of each row. It also compensates for the increased range at the edges of each row. However, although such a scan gives a good plan of the whole area, in some cases it is possible to predict in which locations, if any, the leaks will occur, e.g. where there are spaced units of machinery handling compressed gases. Under such circumstances, it may be more advantageous to direct the beam at and stop on those separate locations in turn, or to pause on those locations during a full raster scan so as to give a higher weighting to the monitoring of those more-vulnerable areas.

It is further preferred to display the results of the monitoring by showing on the screen of a visual display unit, a plan of the area scanned with an indication of the amount of detected gas superimposed.

Figure 2:
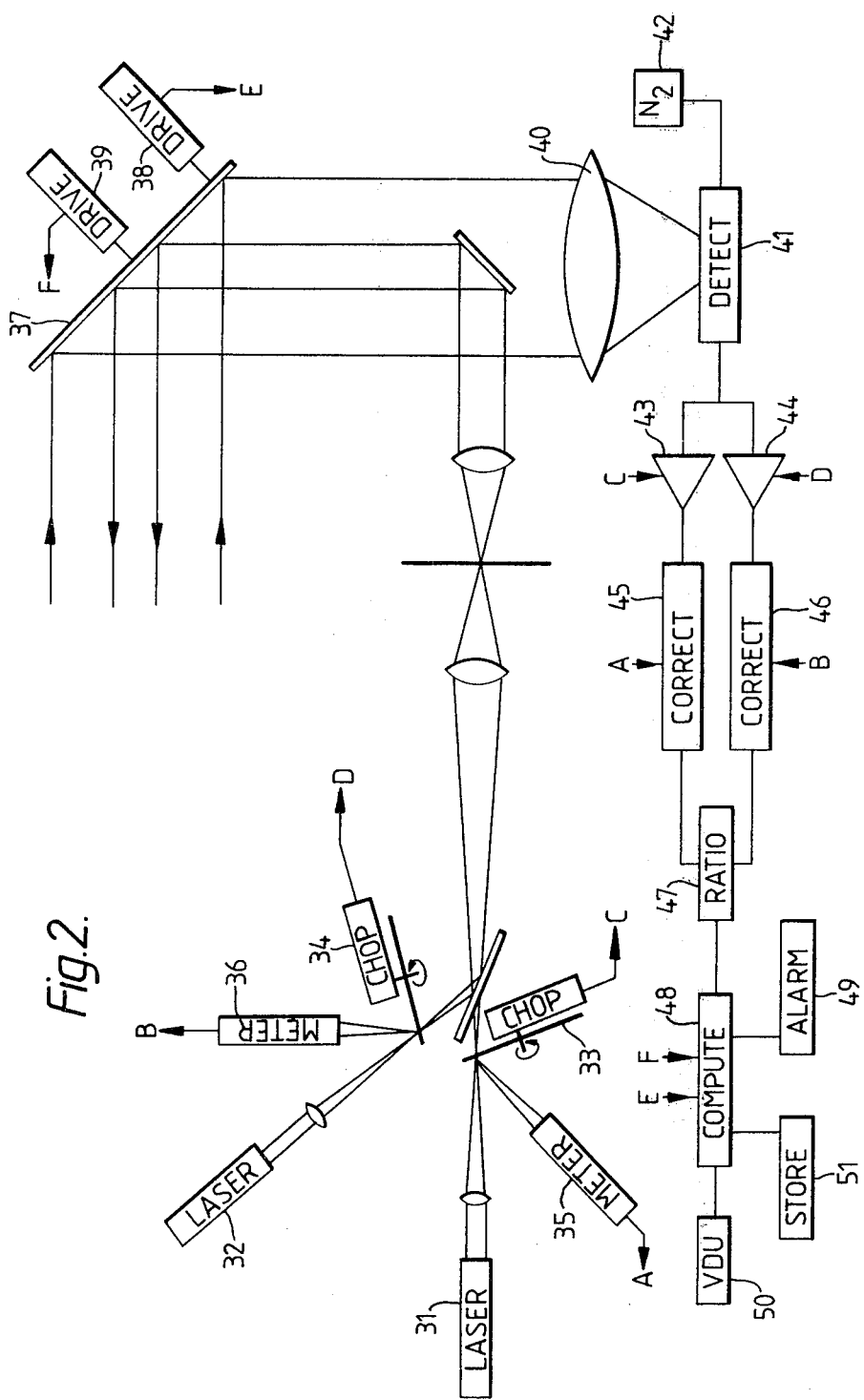

The invention is illustrated by reference to two specific embodiments thereof, shown in the accompanying drawings in which:

FIG. 1 shows a prototype apparatus for monitoring ethylene in the atmosphere around a polythene plant and FIG. 2 shows a further apparatus which differs from that of FIG. 1 in a few details. Both drawings are diagrammatic views, each showing the apparatus in operation.

The apparatus of FIG. 1 comprises two continuous mode carbon dioxide $C^{12}O_2^{16}$ lasers, 1, 2, each emitting about 10 W, which are operated by a high voltage power supply 3. One laser 1 is grating-tuned to a wavelength of 9.227 $\mu$m in the infra-red, this being a wavelength at which there is very little absorption by ethylene (absorption coefficient = 0.046 cm$^{-1}$ bar$^{-1}$), this laser is used for providing the reference beam. The other laser 2 is grating-tuned to a wavelength of 10.258 $\mu$m in the infra-red, at which wavelength there is much stronger absorption by ethylene (absorption coefficient 0.55 cm$^{-1}$ bar$^{-1}$), and this laser is used to provide the detection beam. The reference beam is steered by gold mirrors 4, 5 and then focussed by an anti-reflection coated germanium lens 6 through a rotating sector chopper 7 which mechanically interrupts the reference beam at a frequency near 3kHz. The detection beam is steered by gold mirrors 8, 9 and then focussed by an anti-reflection coated germanium lens 10 through a rotating sector chopper 11 which mechanically interrupts the detection beam at a frequency near 3kHz, but which differs from the frequency at which the reference beam is modulated. Typically, the detection and reference beams are modulated at 3kHz and 2.7 kHz respectively. The blades of the choppers 7, 11 are gold plated to reflect the radiation which does not pass between the blades, onto thermopile power meters 12, 13 which serve to monitor continuously the laser power.

The detection and reference beams are then combined using a slab 14 of germanium mounted in a vertical plane at the Brewster angle so that it transmits approximately 99% of the horizontally-polarised reference beam and reflects approximately 70% of the vertically-polarised detection beam, to give a combined co-incident beam.

The combined beam then passes through a reverse telescope comprising anti-reflection coated germanium lenses 15, 16 which expand the beam. A removeable pin hole 17 is used as a simple spatial filter to aid adjustment. Typically, the telescope gives a beam divergence of 10 mrad, whereby the spot diameter at 100 m distance will be 1 m, and the average power level will be only 1 mW cm$^{-2}$. This power level is much less than the infra-red radiation from a human body or even from the ground itself, and is well within the continuous exposure allowed under British Specification No. 4803.

The beam is turned by an elliptical gold mirror 18 mounted in a telescope having a parabolic mirror 19, and then directed towards the desired locations around the polyethylene plant by a flat gold mirror 20 which is steered by two motors (not shown) so that it can be angularly displaced about both horizontal and vertical axes. To aid initial alignment, a mirror 21 is provided, which may be inserted temporarily into the beam, and a telescopic gun sight 22 used to view the locations towards which the beam is directed, using the same optical system.

A small fraction of the radiation directed at the various locations is scattered back in the direction of the apparatus, and reflected by the gold mirror 20 onto the parabolic mirror 19 which condenses the radiation via mirror 18 and the focussing lens 23 onto a liquid-nitrogen-cooled cadmium mercury telluride photoconductive detector 24.

The electrical signal resulting from the detector 24 is fed to a preamplifier 25, and the preamplified signal resulting therefrom is fed to two lock-in amplifiers 26, 27 which take a reference from choppers 7, 11 respectively, and are thereby made sensitive to the part of the signal having the respective modulation frequencies corresponding to the reference beam and the detection beam. The two outputs of the lock-in amplifiers 26, 27 are coupled to an electronic logarithmic ratiometer 28 and its output is displayed on a meter 39.

As the ratiometer is logarithmic, the relationship between its output and the mass of gas through which the beam has travelled is linear.

The apparatus shown in FIG. 2 is very similar to that of FIG. 1 in overall structure. Two uprated continuous mode carbon dioxide $C^{12}O_2^{16}$ lasers 31, 32 are used, each having its own integral power supply and each being capable of emitting 40 W power. These provide respectively a detection beam at 9.673 $\mu$m (absorption coefficient = 2.15 cm$^{-1}$ barthu $-1$) and a reference beam at 9.619 $\mu$m (absorption coefficient = 0.24 cm$^{-1}$ bar$^{-1}$). The beam is again passed through choppers 33, 34 with light reflected from the back of the chopper blades being directed to power meters 35, 36. The power meters 35, 36 continuously monitor the power output of the lasers 31, 32 and give out signals A and B which are a measure of the laser power. The choppers also give out signals C and D indicative of their rates of rotation and hence of the frequencies at which the respective beams are being chopped. The beams after modulation by the choppers, are combined using a slab of germanium set at the Brewster angle and the combined beam is directed towards the various locations using essentially the same optical system as that shown in FIG. 1 except that polished stainless steel mirrors are used instead of gold mirrors. The large mirror 37 is positioned angularly with respect to the combined beam by two drive motors 38, 39 which tilt the mirror about a horizontal axis and about an axis perpendicular to that horizontal axis, respectively. The angular displacements are measured by shaft encoders on the drive units, and these measurements are given out as signals E and F respectively.

Instead of using a mirror to focus the scattered radiation collected by the telescope (as in FIG. 1) this apparatus uses a lens 40, which focusses the light directly onto liquid nitrogen cooled detector 41, having automatic topping-up means 42 for the cooling liquid. The output from the detector is divided and fed to two lock-in amplifiers 43, 44 taking signals C and D from the choppers to provide a continuous reference for the frequency selection. These amplifiers isolate the two modulated signals, which are smoothed and then corrected for power fluctuations in their respective originating lasers, by ratiometers 45, 46 using signals A and B from the power meters as their references. The corrected signals are then compared in a further ratiometer 47, and the ratio obtained is fed to a computer 48.

The computer effectively does two jobs. One is to compare the ratio signal from the ratiometer 47 with a preset standard representing the tolerable gas limit and to sound an alarm 49 when the ratio drops below that limit, i.e. when the mass of gas exceeds the tolerable limit. The other purpose is to display on a visual display unit 50, a plan of the area of the polyethylene plant being scanned, superimposed with an indication of the level of ethylene detected, with a continuous up-dating of the display. To do this, the signals E and F from the mirror drives are input into the computer as an indication of the orientation of the mirror 37 and hence of the location on the plant to which the signal from the ratiometer 47 at any instant, relates.

The computer of this apparatus is also provided with a store 51 in the form of a floppy disc which records continuously the data fed to the visual display unit, the data being stored for a period of 75 minutes before being erased on the introduction of fresh data. This predetermined period was found to be convenient for this application in that it enabled a record of the build up of any leak to be analysed later. The most appropriate periods for storing the data depend on the particular application, but generally lie within the range of 0.5 to 1.5 hours. The store may also have means to freeze the data in the store when a gas leak is detected.

The apparatus is mounted on a tall tower overlooking the polyethylene plant, but outside the hazard area. The total area scanned is about 100 m by 150 m, and the beam is directed downwards as it scans this area from the tower. Much of the radiation is scattered by the ground, but other scattering surfaces include buildings and pipework. The diameter of the beam when it hits the ground or plant buildings is between 1 and 2 m depending on range and there are roughly 3000 individual locations to be scanned. The response time of the complete system is about 3 ms. This enables the whole area to be scanned in 30 seconds while giving a residence time for each location in at least part of the beam of about 10 ms. Even though heterodyne techniques cannot be used for improving the signal to noise ratio with a scanning beam of this type, the simple techniques employed here have been found to be both rapid and sensitive in the detection of escaping ethylene, and the apparatus has proved to be both reliable and robust.

What we claim is:

1. Apparatus for remote quantitative monitoring of one or more selected gases in a gaseous environment which comprises:

laser sources for generating electromagnetic radiation capable of being tuned to give at least one detection beam containing a specific absorption wavelength of the gas or gases to be monitored and at least one reference beam having a wavelength that is significantly less strongly absorbed by the gas or gases to be monitored, means for modulating the amplitude of each of the beams with different modulation frequencies or phases, means for combining the modulated beams into a single combined beam in which the component beams are substantially coincident with one another, scanning means to displace the combined beam angularly through the gaseous environment so as to direct the beam towards a plurality of locations sequentially and repetitively, means for collecting at least a portion of the radiation which is returned from each of the locations, a detector for deriving electrical signals corresponding to the intensity of the collected radiation, means for isolating the electrical signals corresponding to the intensity of the radiation having the aforesaid modulation frequencies or phases, means for obtaining the ratio of the isolated signals corresponding to radiation collected from a detection beam and a related reference beam thereby to provide a measure of the amount of the selected gas or gases in each beam path traversed between the apparatus and the scanned locations, and means for indicating the amount of gas detected.

2. Apparatus as claimed in claim 1 characterised in that the laser sources for both detection and reference beams are continuous mode gas lasers.

3. Apparatus as claimed in claim 1 or claim 2 characterised by having two lasers of which one is for providing the detection beam and the other is for providing the reference beam, the lasers being tuned to wavelengths in the infra-red which differ by less than 0.1 $\mu$m.

4. Apparatus as claimed in claim 1 characterised in that the means for combining the modulated beams comprises a slab of material transparent to the two beams mounted such that the two beams will strike opposite sides of the slab at the Brewster angle with mutually perpendicular planes of polarisation, whereby one beam will be transmitted and the other will be predominantly reflected to form two substantially coincident beams distinguishable by their different modulations.

5. Apparatus as claimed in claim 1 characterised in that the scanning means is moveable in at least two directions so as to direct the combined beam at locations which are spread over an area whose dimensions in any two perpendicular directions is greater than the width of the beam.

6. Apparatus as claimed in claim 5 characterised in that the scanning means comprises a mirror mounted within the path of the combined beam and moveable angularly relative to the incident combined beam so as to direct the beam towards different locations when such angular movement occurs.

7. Apparatus as claimed in claim 6 characterised in that the scanning means incorporates means for cleaning the surface of the mirror.

8. Apparatus according to claim 1 characterised in that there is also provided means to compensate each of the isolated signals for any fluctuations in the power output of the relevant beam.

9. Apparatus according to claim 1 characterised in that the means for indicating the amount of gas detected comprises an alarm system arranged to operate when the ratio of the signals exceeds a predetermined threshold.

10. Apparatus according to claim 9 characterised in that the indicating means also provides an indication of the location being monitored when the threshold is exceeded.

11. Apparatus according to claim 1 characterised in that the indicating means comprises computing means having inputs of at least the ratio of the isolated signals and the position of the scanning means, and being programmed to derive from these inputs an accessible correlation between the amounts and the positions of the selected gas or gases detected while continuously updating this correlation as monitoring proceeds.

12. Apparatus according to claim 11 characterised in that the computing means has a visual display unit for showing the correlation of gas amounts and positions by superimposing an indication of the amount of gas detected onto a plan of the area scanned.

13. Apparatus according to claim 12 characterised in that the computing means is provided with a store into which the data displayed on the visual display unit may be continuously fed, the data being stored for a predetermined period before being erased on the introduction of fresh data into the store.

14. A method for remote quantitative monitoring of one or more selected gases in a gaseous environment which comprises the steps of:

generating electro-magnetic radiation from laser sources to give at least one detection beam containing a specific absorption wavelength of the gas or gases being monitored and at least one reference beam having a wavelength that is significantly less strongly absorbed by the gas or gases being monitored;

modulating the amplitude of each of the beams with different modulation frequencies or phases, combining the modulated beams into a single beam in which the component modulated beams are substantially coincident with one another, displacing the combined beams angularly through the gaseous environment so as to direct the combined beam towards a plurality of locations sequentially and repetitively, collecting at least a portion of the radiation which is returned from each of the locations, deriving electrical signals corresponding to the intensity of the collected radiation, isolating the electrical signals corresponding to the intensity of the radiation having the aforesaid modulation frequencies or phases and, obtaining the ratio of the isolated signals corresponding to radiation collected from a detection beam and a related reference beam thereby to provide a measure of the amount of the selected gas or gases in each beam path traversed by the collected radiation originating from the laser sources.

15. A method as claimed in claim 14 characterised in that it comprises angularly displacing the combined beam continuously so as to direct the beam at successive locations in a pattern wherein the beam traverses substantially parallel rows of locations sequentially and in alternate directions, the rate at which the beam traverses each row being varied with distance along the row such that the beam executes simple harmonic motion.

16. A method as claimed in claim 14 or claim 15 characterised in that it comprises displaying the results of the monitoring by showing on the screen of a visual display unit a plan of the area scanned with an indication of the amount of detected gas superimposed.

* * * * *